United States Patent
Stimpfl et al.

(10) Patent No.: US 7,710,550 B2
(45) Date of Patent: May 4, 2010

(54) OXIMETER FOR SPECTRO-PHOTOMETRIC IN-VITRO DETERMINATION OF HEMOGLOBIN DERIVATIVES

(75) Inventors: Peter Stimpfl, Graz-Neuhart (AT); Herfried Huemer, Feldbach (AT); Manfred Strohmeier, Graz (AT); Stefan Untersberger, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/112,163

(22) Filed: Apr. 30, 2008

(65) Prior Publication Data

US 2008/0274554 A1 Nov. 6, 2008

(30) Foreign Application Priority Data

May 3, 2007 (EP) .................. 07450085

(51) Int. Cl.
*G01N 33/48* (2006.01)
(52) U.S. Cl. ...................................... 356/41
(58) Field of Classification Search ............ 356/41, 356/39, 40
See application file for complete search history.

(56) References Cited

U.S. PATENT DOCUMENTS

| | | | |
|---|---|---|---|
| 5,353,790 A | 10/1994 | Jacques et al. | |
| 5,515,864 A * | 5/1996 | Zuckerman | 600/311 |
| 6,262,798 B1 | 7/2001 | Shepherd et al. | |
| 6,373,574 B1 | 4/2002 | Gu et al. | |
| 6,393,310 B1 | 5/2002 | Kuenstner | |
| 6,711,426 B2 | 3/2004 | Benaron et al. | |
| 6,809,347 B2 | 10/2004 | Tasch et al. | |
| 6,882,425 B1 * | 4/2005 | Elsenhans et al. | 356/436 |

(Continued)

FOREIGN PATENT DOCUMENTS

DE 29724848 U1 11/2004

(Continued)

OTHER PUBLICATIONS

DeAbreu et al. ("Total Bilirubin Assay on GEM®PremierTM 4000 Critical Care Analyzer", Poster, AACC Annual Meeting, Jul. 15-19, 2007).*

(Continued)

*Primary Examiner*—Roy Punnoose
(74) *Attorney, Agent, or Firm*—McDonnell Boehnen Hulbert & Berghoff LLP

(57) ABSTRACT

An oximeter for spectro-photometric in-vitro determination of hemoglobin derivatives in a sample, typically a hemolyzed blood sample, is provided comprising a single measurement light source emitting measurement radiation, a sample chamber, for instance a measurement cuvette containing the sample, a detector device, which records a spectrum of the measurement radiation after its interaction with the sample, and an evaluation unit following the detector device, which determines the hemoglobin derivatives and at least one further analyte from the spectrum recorded by the detector device. The measurement light source is a polychromatic LED, which for determination of hemoglobin derivatives emits measurement radiation in at least one spectral region B, in which the hemoglobin derivatives exhibit significant absorbance, and which for determination of the at least one further analyte emits measurement radiation in at least one other spectral region A, in which the at least one further analyte exhibits significant absorbance.

22 Claims, 3 Drawing Sheets

U.S. PATENT DOCUMENTS

| | | |
|---|---|---|
| 2002/0020748 A1 | 2/2002 | Gu et al. |
| 2005/0127358 A1 | 6/2005 | Kawamura |
| 2005/0127385 A1 | 6/2005 | Reeh et al. |
| 2005/0154277 A1 | 7/2005 | Tang et al. |
| 2005/0267346 A1 | 12/2005 | Faber et al. |
| 2007/0015981 A1 | 1/2007 | Benaron et al. |

FOREIGN PATENT DOCUMENTS

| | | |
|---|---|---|
| DE | 10360563 A1 | 7/2005 |
| EP | 1447658 A1 | 8/2004 |
| EP | 1473771 A1 | 11/2004 |
| EP | 1475835 A2 | 11/2004 |
| JP | 2004108781 | 4/2004 |
| WO | 2004070369 A1 | 8/2004 |
| WO | 2005084527 A1 | 9/2005 |
| WO | 2006086085 A2 | 8/2006 |
| WO | WO 2007033318 (A2) | 3/2007 |
| WO | 2007003318 A2 | 11/2007 |

OTHER PUBLICATIONS

Zheng et al ("In Vitro Determination of Bilirubin in Hemolysed Whole Blood Using First Derivative Analysis", Proceedings—19th International Conference—IEEE/EMBS Oct. 30-Nov. 2, 1997, Chicago, Illinois, U.S.A. pp. 2384-2387).*

Boalth, Nicolas, et al., "Blood gases and oximetry: calibration-free new dry-chemistry and optical technology for near-patient testing," Clinica Chimica Acta 307 (2001) 225-233.

Hallemann, H. et al., "Technical Aspects of Bilirubin Determination in Whole Blood," Point of Care 4;1 (Mar. 2005) 9-10.

DeAbreu et al., "Total Bilirubin Assay on GEM®Premier™ 4000 Critial Care Analyzer", Poster, AACC Annual Meeting, Jul. 15-19, 2007.

Pamidi et al., "Analytical Performances of Co-Oximetry Module on GEM®Premier™ 4000 Critical Care Analyzer", Poster, AACC CPOCT Symposium, Sep. 28-30, 2006.

Pamidi et al., "Analytical Performances of Co-Oximetry Module on GEM®Premier™ 4000 Critial Care Analyzer", Point of Care, vol. 6, No. 1, p. 96, Mar. 2007.

JP 2004-108781, Published Apr. 8, 2008, concise explanation provided in paragraph [003] of the specification.

* cited by examiner

OXIMETER FOR SPECTRO-PHOTOMETRIC IN-VITRO DETERMINATION OF HEMOGLOBIN DERIVATIVES

BACKGROUND OF THE INVENTION

The present invention relates to oximeters for spectro-photometric in-vitro determination of hemoglobin derivatives and at least one further analyte in a sample.

Currently available oximeters mainly use incandescent lamps as measurement light sources. In "Technical Aspects of Bilirubin Determination in Whole Blood"; HALLEMANN et al.; Point of Care Volume 4, Number 1, March 2005, an oximeter module of a blood gas analyzer (OMNI Blood Gas Analyzer) is described, in which bilirubin is spectroscopically determined as an additional analyte beside hemoglobin derivatives. A halogen lamp with a broad spectral range is used as a measurement light source.

From JP 2004-108781 a spectroscope has become known, in which prior to irradiation into a sample, light emitted by a white light LED is split into its spectral components by means of two diffraction gratings and is then radiated into the sample through a projection slit, in order to determine an analyte in a sample, for instance. Variants based on a transmission geometry as well as variants based on a reflection geometry are described, where the intensity of transmitted or reflected light is measured in temporal sequence for each wavelength. A disadvantage of this known spectroscope is the time-consuming recording of a spectrum by means of the two diffraction gratings, which split the measuring light into its spectral components.

From U.S. Pat. Appln. Pub. No. 2005/0154277 A1 a miniaturized "in-vivo" spectroscope is known, which can be used inside the body for instance to detect hemorrhages in the gastrointestinal tract by means of spectral analysis of the hemoglobin derivatives present. LEDs may be used as light source.

Furthermore, use of a non-invasive oximeter is known from U.S. Pat. Appln. Pub. No. 2005/0267346 A1, where light is radiated into blood-filled tissue of a fingertip or earlobe, and the composition of the blood (oxygen saturation) is inferred from light-absorption in the blood using a transmitted-light or reflected-light method. A white light LED can be used as light source, but filters or diffraction gratings must be used prior to irradiation to select defined wavelengths for irradiation into the tissue.

From U.S. Pat. No. 6,262,798 B1 an oximetric method for measuring non-hemolyzed blood is known. In this measurement method a plurality of defined, monochromatic wavelengths are sequentially radiated into the sample, arrays of varicolored LEDs or conventional white light lamps being used from which defined wavelengths are filtered by means of a monochromator, which are then radiated into the sample.

In "Blood gases and oximetry: calibration-free new dry-chemistry and optical technology for near-patient testing"; Boalth et al.; Clinica Chimica Acta 307 (2001) 225-233, a spectrophotometric system for in-vitro oximetry is described, which works with a white light LED as light source. For the determination of hemoglobin derivatives the wavelength band of 470-670 nm is recorded by means of a 128-channel-linear-CCD-array and used for evaluation. This wavelength range exceeds the wavelength range conventionally used for determination of hemoglobin derivatives, thus offering the possibility of correcting the values of hemoglobin derivatives for bilirubin as an interfering substance, which overlays hemoglobin absorption in parts of the range. The enlarged wavelength range is only used for correcting the hemoglobin derivatives to be determined, but not for determining bilirubin as an additional analyte.

To produce polychromatic light by means of LEDs, it has become known to use luminescence conversion LEDs having one or more primary emission wavelengths, which are modified by luminescence conversion layers such that broad-band polychromatic light will be radiated as a result. Such light sources are for instance described in U.S. Pat. Appln. Pub. No. 2005/0127385 A1. The radiated polychromatic light is in this case composed of a short-wave spectral region of the primary emission wavelengths emitted by at LED-chip as primary emitter, and a spectral region of longer wavelengths radiated by dye layers excited by the primary emission of the LED as secondary emitters.

U.S. Pat. No. 6,809,347 B2 describes a white light LED which includes a LED emitting blue or UV-light and a superposed luminophore layer which absorbs part of the blue or UV-light emitted by the LED and subsequently emits light in the long-wave spectral region, thus producing white light by superposition, whose spectral characteristics can be defined by modification of the luminophore layer.

Finally, EP 1 473 771 A1 describes an alternative design of a white light LED, which consists of a plurality of at least partially transparent light-emitting LED layers of different emission wavelengths, which are stacked one above the other in such a way that the individual emission wavelength bands are superposed in radiation direction and white light is emitted as a result.

SUMMARY OF THE INVENTION

It is against the above background that the present invention provides certain unobvious advantages and advancements over the prior art. In particular, the inventors have recognized a need for improvements in oximeters for the spectro-photometric in-vitro determination of hemoglobin derivatives and at least one further analyte in a sample.

Although the present invention is not limited to specific advantages or functionality, it is noted that the present invention provides an oximeter for the spectro-photometric in-vitro determination of hemoglobin derivatives, typically in a medical sample, in such a way that a compact measuring module is achieved, which will permit fast recording of the measured spectra as well as determining further analytes besides hemoglobin derivatives. Furthermore, sufficient stability (little drifting) and long service life of the light source is ensured. The oximeter of the present invention exhibits greater ease of use, less maintenance due to prolonged service life of the light source and high accuracy of the measured results.

The present invention is directed to an oximeter for spectro-photometric in-vitro determination of hemoglobin derivatives and at least one further analyte in a sample, typically a hemolyzed blood sample, the oximeter comprising a single light source emitting measurement radiation, and a sample chamber, for instance a measurement cuvette receiving the sample, and a detector device recording a spectrum of the measurement radiation after its interaction with the sample, and an evaluation unit following the detector device, which determines the hemoglobin derivatives and at least one further analyte from the spectrum obtained by the detector device.

In accordance with one embodiment of the present invention, an oximeter for spectro-photometric in-vitro determination of hemoglobin derivatives and at least one further analyte in a sample is provided comprising a single measurement light source, a detector device, and an evaluation unit following the detector device. The single measurement light source, which emits measurement radiation, is directed to a sample chamber containing the sample. The detector device records a spectrum of the measurement radiation after its interaction with the sample. The evaluation unit following the detector device determines the hemoglobin derivatives and at least one further analyte from the spectrum recorded by the detector device. The measurement light source is a polychromatic LED, which for determining the hemoglobin derivatives emits measurement radiation in at least one spectral region B in which the hemoglobin derivatives exhibit significant absorbance, and which for determining the at least one further analyte emits measurement radiation in at least one other spectral region A in which the at least one further analyte exhibits significant absorbance.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
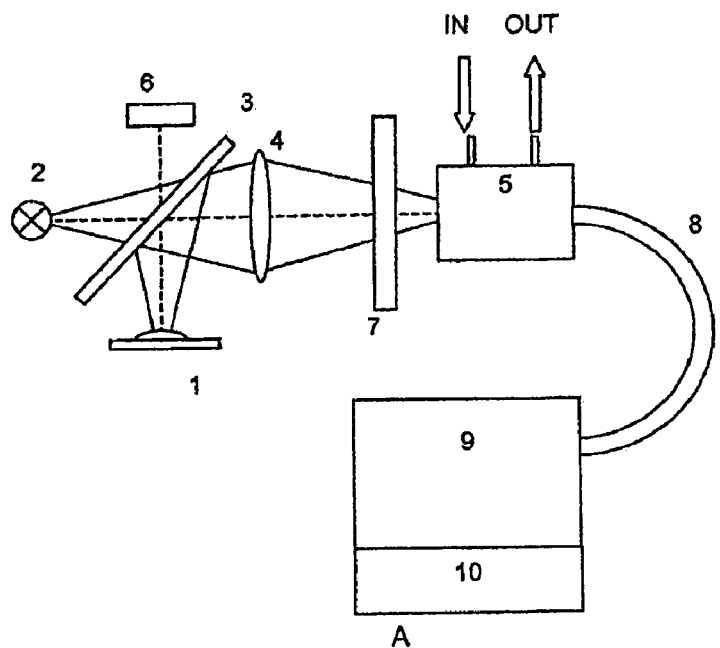
FIG. 1 shows a schematic of an oximeter according to an embodiment of the present invention.

Skilled artisans appreciate that elements of the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

In accordance with the present invention, the measurement light source can be a polychromatic LED, which for determination of hemoglobin derivatives emits measurement radiation in at least one spectral region B, where hemoglobin derivatives show significant absorbance, and for determination of at least one additional analyte emits measurement radiation in at least one other spectral region A, where the at least one additional analyte shows significant absorbance. Significant absorbance of the measurement radiation is provided such that in multicomponent analysis, for instance, absorbance values by the hemoglobin derivatives and by the other analyte are sufficiently differentiable. Suitable spectral regions are for instance in the range of 520-670 nm for determination of hemoglobin derivatives and in the range of 450-500 nm for determination of bilirubin.

The term "polychromatic LED" essentially refers to a white light LED, for instance as described in the above cited U.S. Pat. Appln. Pub. No. 2005/0127385 A1, U.S. Pat. No. 6,809,347 B2 or EP 1 473 771 A1, whose emission wavelength region and intensity curve are adapted to the absorption characteristics of the hemoglobin derivatives to be determined and, if required, are extended for determination of an additional analyte.

According to a first variant of the invention the measurement light source may be a luminescence conversion LED, which comprises at least one primary and at least one secondary emitter, the primary emitter emitting in the spectral region A and the secondary emitter emitting in the spectral region B.

In a typical variant of the present invention based on a luminescence conversion LED, the spectral curve (light intensity as a function of wavelength) is defined by the choice of type, number and amount of the phosphors employed, and by a suitable choice of excitation wavelength (type and number of primary emitters), and is optimally adjusted to the analytes to be determined in the sample. This design of the measurement light source has the further advantage over conventional light sources that the emitted light has an essentially homogeneous spectrum across the output surface of the light source, which is employed in measurement or over the output radiation angle range of the light source, which is employed in measurement. Such emission characteristics are factors for the reduction of tolerance sensitivity as regards the positioning of the optical components of the measuring system of the oximeter. It is especially the size of the radiating area of the LED which compares favorably with that of a conventional halogen lamp, so that a high tolerance of alignment errors of the optical system of the oximeter may be achieved.

According to another variant of the present invention, the measurement light source comprises a plurality of light emitting layers with different emission spectra, where at least one of the light emitting layers emits measurement radiation in the spectral region A and at least one other light emitting layer emits measurement radiation in the spectral region B, and where the light emitting layers are positioned relative to each other within the measurement light source in such a way that the measurement radiation has an essentially homogeneous spectrum across the output surface of the light source, which is utilized in measurement or over the output radiation angle range of the light source, which is utilized in measurement.

According to this variant it will also be possible to use individual light emitting layers or single emitters (SMD or conventional LEDs) for the generation of measurement radiation, provided they are placed in sufficiently close proximity to each other, such that the measurement radiation utilized in measurement has an essentially homogeneous spectrum across the output surface of the measurement light source. The spectral curve can be defined via type and number and operating parameters of the individual light emitting layers or single emitters. The expression "sufficiently close proximity" is to be understood such that the positioning of the optical components will be insensitive to geometric tolerances when the light source radiates through the sample towards a detector unit. Thus intensity as well as spectrum of the detected light will not significantly change, even if deviations from the ideal positioning of the relevant optical components (i.e., the alignment of the optical components along the optical axis) occur. This will advantageously result in a system which is significantly more robust against and less prone to misalignments.

The invention utilizes a polychromatic LED for spectrometric determination of all hemoglobin derivatives and at least one other substance. Such other substances will exhibit light absorption outside the absorption region of the hemoglobin derivatives, which can be utilized for their spectrometric determination.

An example of such an analyte is bilirubin, which can for instance be determined via its absorption in the wavelength range of 450-500 nm (corresponding to spectral region A of the measurement radiation).

An especially suitable spectral region for determination of hemoglobin derivatives will be the wavelength region of 520-670 nm (corresponding to spectral region B of the measurement radiation).

According to yet another variant of the invention, the measurement light source comprises a plurality of light emitting layers with different emission spectra, which layers are at least partially transparent and are arranged in a stack in such a way that due to superposition of the emitted radiation of the individual layers a resulting radiation in emission direction is produced, which has a spectral distribution that is essentially homogeneous across the output surface of the measurement light source.

According to a further variant the measurement light source may contain a plurality of light emitting areas or single emitters with different emission spectra, which are arranged in such close proximity to each other that due to superposition of the emitted radiation of the individual areas or single emitters a resulting radiation in emission direction is produced, which has a spectral distribution that is essentially homogeneous across the output surface of the measurement light source.

The emission spectrum of such measurement light source is a sum spectrum and is additively made up of the individual emission spectra of the light emitting layers, where depending on the position of the individual light emitting layers and/or the presence of light attenuating layers within the measurement light source, the emission spectra of the individual light emitting layers may be modified before the emitted light exits from the measurement light source.

The light emitted by the measurement light source can have an essentially homogeneous spectrum across the whole output surface of the measurement light source utilized for measurement or over the output radiation angle of the measurement light source utilized for measurement. The output surface of the measurement light source utilized for measurement or the output radiation angle of the measurement light source utilized for measurement are to be understood as the area of the output surface of the measurement light source which is irradiated into the sample by the optical system of the oximeter and is finally mapped onto the detector device. The spectral distribution of the emitted measurement radiation should be as homogeneous as possible especially across this area. Homogeneous spectral distribution across an area in this instance means that light is emitted from all points of the area, its spectral distribution being the same for each point of emission (identical emission wavelength ranges and identical intensity of the radiation emitted at a particular wavelength).

The light emitted by the measurement light source is irradiated into the sample chamber, which contains the sample to be analyzed. There the irradiated light interacts with the substances contained in the sample in such a way that, depending on the type and concentration of these substances (especially the substances to be analyzed), the spectral composition of the light emitted by the measurement light source will change. This is essentially due to substance-specific absorption of the light emitted by the measurement light source in certain wavelength bands. The spectrum of the measurement light modified by the sample is recorded by means of a suitable detector device. Either a transmitted-light method or a reflected-light method may be used in this context. In both methods it is of advantage if the detector device, possibly in cooperation with a following evaluation unit, records in one measurement step a spectrum of the light of the measurement light source specifically modified by interaction with the sample, from which the hemoglobin derivatives and the at least one further analyte can be determined. Recording of the spectrum is preferentially carried out simultaneously by means of a detector array. It would also be possible, however, to record the spectrum by a sequential technique. In both cases the result of the detecting step is a single spectrum which can be evaluated.

The spectrum recorded by the detector device is processed in the evaluation unit in such a way that hemoglobin derivatives and the at least one further analyte can be determined. For this purpose various methods are known to experts in the field, for instance multicomponent procedures.

The geometrical emission characteristics of the measurement light source can be further modified in an advantageous way by providing light-scattering diffusor layers for homogenization of the radiated measurement light. Such diffusor elements may be located as integral components within the measurement light source or as separate optical elements in the optical path outside the light source.

The design of the measurement light source according to the invention advantageously meets the requirements for spectral adaptation of the measurement radiation as regards optimization of the signal/noise ratio over the complete spectral range taking into account analyte absorption and optimization of wavelength-dependent stray light in the detector device by suitable choice of type, number and amount of primary and secondary emitters.

The oximeter may also include further optical components such as filters, light guides, lenses, beam splitters, diffuser elements, etc. for guiding and propagating the measurement radiation from the measurement light source to the sample chamber and/or from the sample chamber to the detector device.

It is proposed especially that the detector device includes a polychromator followed by a multi-channel detector unit, for instance a detector array which simultaneously records all measurement wavelengths. This will result in great advantages in comparison with sequential measurement, as in the initially cited JP 2004-108781, above all significantly shorter measurement time and the avoiding of mechanically moving parts (diffraction gratings, etc.).

Filters or other optically absorbing media may be used between measurement light source and sample chamber and/or between sample chamber and detector device for further adaptation of the spectrum. To avoid stray light in the detector device and to minimize heating up of the sample and/or the optical system of the oximeter certain wavelength bands of the light emitted by the measurement light source, which are of lesser analytical relevance, may for instance be filtered out at least partially. These additional elements may be designed either as integral components of the measurement light source or as separate optical elements following the measurement light source.

It is of advantage if the spectral bands of the measurement radiation used for determining hemoglobin and the at least one other analyte are separated by a region of lower intensity, especially if only little analytically relevant information is contained in this region.

The term oximeter as used in the present application in general implies a spectrometer which will permit at least the different hemoglobin derivatives to be determined by their different absorbance properties, and especially such hemoglobin derivatives as oxyhemoglobin (O2Hb), deoxyhemoglobin (HHb), carboxyhemoglobin (COHb) and methemoglobin (MetHb).

The advantages of polychromatic LEDs according to the invention over conventional incandescent lamps are summarized as follows:

Improved stability (less drifting);

smaller dimensions;

less waste heat;

no IR intensity (no IR filter needed);

service life about 100,000 hours (halogen lamps typically 5000 hours);

higher efficiency than incandescent lamps;

higher luminosity factor;

continuous operation possible on account of long service life;

intensity is variable over a wide range by varying the current;

no mechanical adjustment of light source required;

intensity control via chip temperature (temperature sensor or contact-free via IR sensor);

spectral adaptation by means of operating current and radiation angle;

application-specific spectrum possible.

The advantages of polychromatic LEDs according to the invention over conventional LEDs (or laser diodes) are as follows:

Like incandescent lamps polychromatic LEDs can be considered as light sources with homogeneous spectrum across the whole output surface: thus simple and low-cost imaging optics possible;

little tolerance-sensitivity;

improved spectral adaptation possible;

simpler, more compact temperature management;

simultaneous determination of additional analytes, for instance bilirubin, together with hemoglobin parameters possible.

The oximeter of the invention is suitable for medical samples containing blood components and possibly a further analyte, for instance bilirubin. This means, e.g., blood samples, in particular hemolyzed whole blood.

The design variants of the invention for a measurement light source may also be freely combined with each other. It is for instance possible to overlay the emission spectra of individual light emitting layers singly or together with suitable luminophore layers which can extend the primary emission spectrum of individual light emitting layers into regions of longer wavelength. Furthermore, luminescence conversion LEDs other light emitting layers or single emitters may be added to extend the spectral band of the emitted light and thus enable determination of additional analytes.

FIG. 1 shows in a schematic representation an exemplary design of an oximeter according to an embodiment of the invention. In the oximeter a polychromatic LED 1 as measurement light source together with a further light source 2 is directly coupled via a beam splitter 3 and a lens system 4 to the sample chamber 5, for instance a measurement cuvette with the blood sample to be analyzed. In this example the further light source 2 is used for wavelength calibration of the oximeter.

The polychromatic LED 1, which radiates broadband measurement radiation of the spectral band 450 to 670 nm into the sample chamber 5, is thermostatted by means of a Peltier element and an NTC temperature sensor. The polychromatic LED is intensity controlled via a control loop with a photodiode 6. The optical system is designed in such a way that adjustment of the polychromatic LED 1 relative to the optical axis will no longer be strictly necessary due to the large output surface of the measurement light source and the essentially homogeneous spectrum across this output surface. Optionally a filter 7 may be inserted between the measurement light source 1 or the beam splitter 3 and the sample chamber 5 to adapt the measurement radiation in the chosen spectral region. The detector device, which is connected to the measurement cuvette 5 via a light guide 8, consists of a polychromator 9, for instance a grating spectrometer and a succeeding multi-channel detector unit 10, e.g., a detector array which simultaneously records all measurement wavelengths. Not explicitly shown in FIG. 1 is the evaluation unit following the detector device, which determines the hemoglobin derivatives and the at least one further analyte from the spectrum recorded by the detector device.

Figure 2:
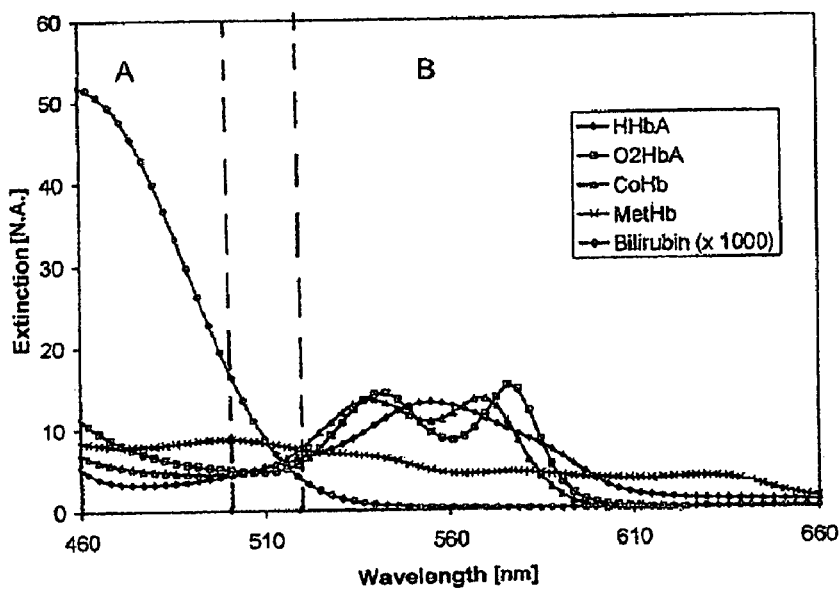
FIG. 2 shows the extinction coefficients of the hemoglobin derivatives O2Hb, HHb, COHb and MetHb and of bilirubin as functions of the wavelength in nm.

The spectral requirements which the measurement light source 1 must satisfy, are in this application dictated by the spectrometer respectively by the analytes to be determined (hemoglobin derivatives and at least one further analyte). Determination of the hemoglobin derivatives and of bilirubin as an exemplary further analyte is based on the extinction coefficients shown in FIG. 2. For the spectrometric determination of the analytes a measurement light source 1 is required which exhibits suitable intensity values in these wavelength bands. For the application at hand the spectrum of the measurement light source 1 should have the following properties:

Downward slope in the long wave region to reduce unwanted stray light in the detector;

an intensity peak in the spectral region B of the absorption maximum of hemoglobin derivatives (520-670 nm);

an intensity peak or at least an intensity sufficient for measurement in the short wave spectral region A (450-500 nm) for determining bilirubin, a region of reduced intensity between the spectral regions A and B.

In order that the invention may be more readily understood, reference is made to the following examples, which are intended to illustrate the invention, but not limit the scope thereof.

EXAMPLES

The following examples are based on an oximeter as shown in FIG. 1. A grating spectrometer 9 with a wavelength resolution of 1.5 nm and with a line sensor 10 with 512 pixels was used. The measurement cuvette 5 forms a fluid channel with a width of 1.0 mm and a layer thickness of 100 μm. The spectral measurement of the polychromatic LED 1 was carried out with an air-filled measurement cuvette. Measurement radiation of the LED was coupled into the measurement cuvette 5 and subsequently into the light guide 8 via a lens 7 (magnification factor 1.6). The light guide 8 is provided as a fiber bundle in order to permit a small curvature radius between measurement cuvette and spectrometer. At the entry point the active diameter of the light guide is 0.7 mm. At the exit end the single fibers of the bundle are arranged linearly, forming the input slit of the spectrometer. The photodiode 6 is used to control the intensity of the LED 1. In this example the LED 1 is combined with another light source 2 (a neon lamp) by means of a beam splitter 3, in order to enable a changeover between two light types (measurement radiation and calibration radiation). Optionally additional filter elements 7 may be used—as mentioned above—for further spectral adjustment of the measurement light source 1.

Example 1

Figure 3:
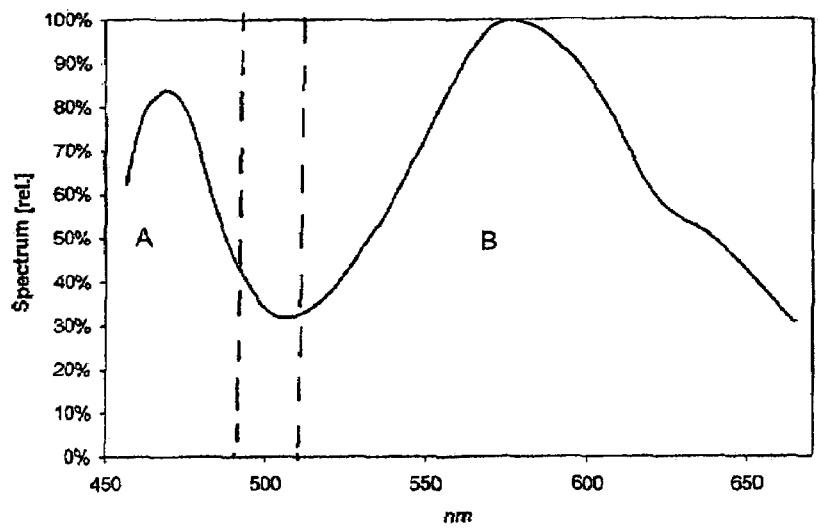
FIGS. 3 to 6 show the emission spectra of diverse polychromatic LEDs.

In the measurement system described above a commercially available white-light LED marketed by Seoul Semiconductor (type: N32180 400 mA 3.5V) was used. The broadband spectrum (see FIG. 3) permits determination of hemoglobin derivatives and bilirubin. The ratio between excitation intensity and luminescence intensity and the intensity decay above 600 nm are suitable for the application.

Example 2

Figure 4:
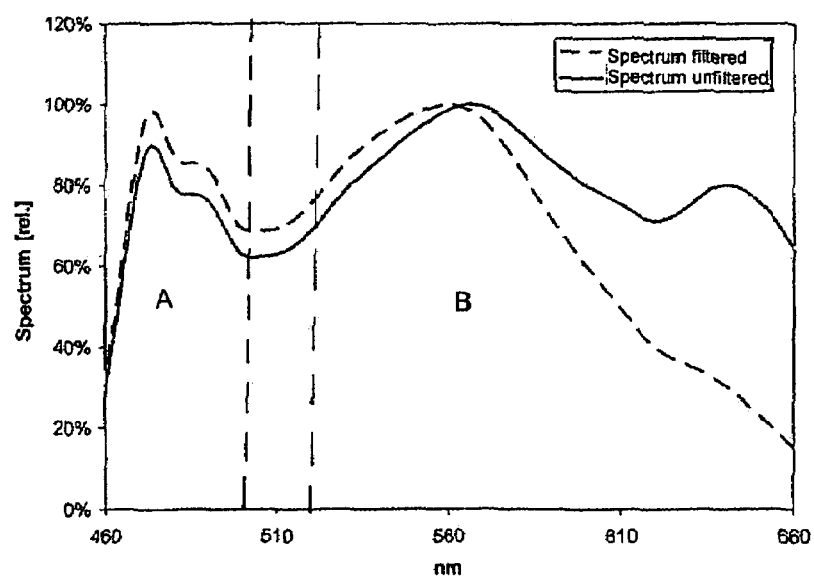

In this example a white light LED of Luxeon (type: LXHL 1 Watt) was used (see spectrum as in FIG. 4). This LED also permits determination of hemoglobin derivatives and bilirubin, but requires the use of additional filters in the long wave band to reduce stray light in the spectrometer. In FIG. 4 the spectrum is shown unfiltered and with filter (Schott BG38, 2 mm). This light source is suitable for the application, in particular in combination with a filter of this kind.

Example 3

Figure 5:
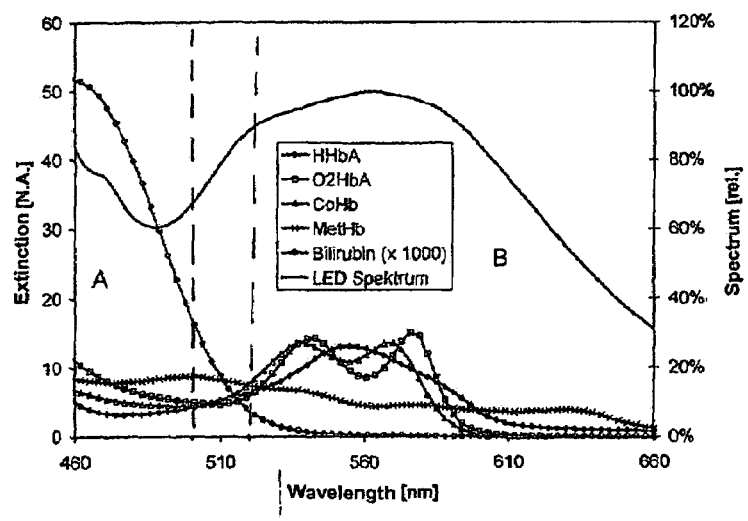

As a typical variant of the present invention, a polychromatic LED with two phosphors and a color temperature of 4000° K. is used. The required spectrum is achieved by using a LED-chip with dominant wavelength 460-462.5 nm, combined with two luminophores (phosphor 1: green, CIE coordinates: x=0.195+/−0.004, y=0.651+/−0.004; phosphor 2: orange, CIE coordinates: x=0.450+/−0.002, y=0.537+/−0.002). The LED has an operating current of 350 mA. In the example the operating current is 100 mA. The spectrum obtained is shown in FIG. 5 together with the extinction coefficients of the analytes. This light source meets all requirements placed on the measurement light source (1). An additional adjustment of the spectrum is not necessary.

Figure 6:
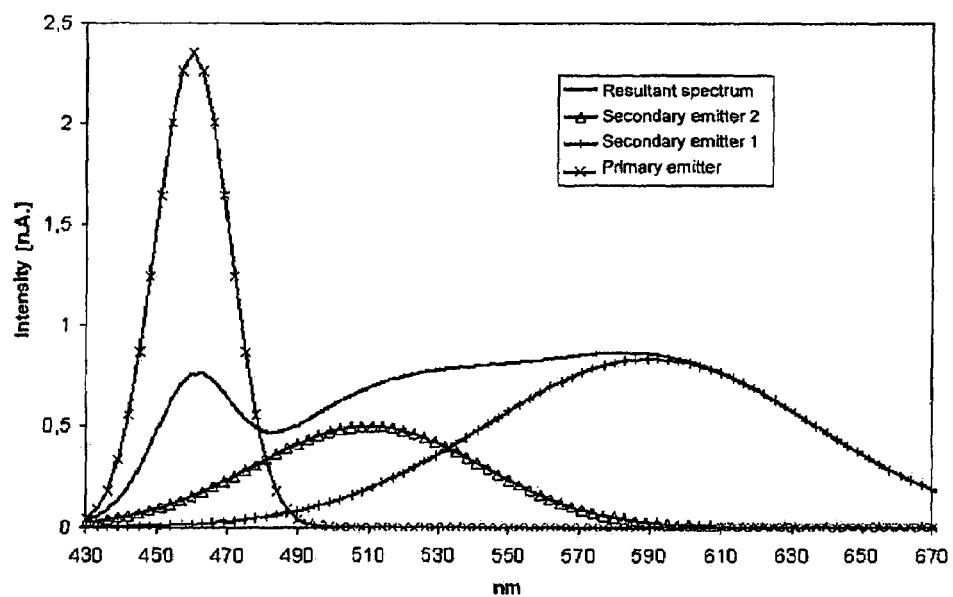

FIG. 6 shows the resultant spectrum of a luminescence conversion LED of this kind based on an example with two luminophores (510 nm and 590 nm) as secondary emitters and a primary emitter emitting at 460 nm. LED chips emitting blue or UV are here combined with luminescence dyes. The dyes are contained in a paste which is applied on the LED chip. The short-wave blue light having higher energy excites the dyes to luminescence, whereupon long-wave light having less energy is emitted. Since not all blue light is converted the resulting additive mixture of spectral colors (the unmarked line in the diagram) produces a polychromatic light with a first narrow-band spectral maximum in the spectral region A at 460 nm and a second broad-band spectral maximum in the spectral region B of 510 to 590 nm. The two regions A and B are separated by a spectral minimum at approximately 485 nm. Here it is of particular advantage that due to the narrow-band emission radiation of the primary emitter a short-wave measurement wavelength region is given for determination of bilirubin via its absorbance peak at 460 nm, and that due to the broad-band emission radiation of the secondary emitter a broad long-wave region is established in which all hemoglobin derivatives to be determined absorb significantly and show absorbance maxima.

According to the invention the spectrum of such polychromatic luminescence conversion LEDs may thus be specifically tuned for determination of further analytes by the choice of the primary emitter (the LED-chip emitting in the spectral region A) and by the choice and combination of diverse luminophores (secondary emitters emitting in the spectral region B).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An oximeter for spectro-photometric in-vitro determination of hemoglobin derivatives and at least one further analyte in a sample comprising:
   a single measurement light source, which emits measurement radiation, being directed to a sample chamber containing a sample,
   a detector device, which records a spectrum of the measurement radiation after its interaction with said sample, and
   an evaluation unit following the detector device, which determines the hemoglobin derivatives and at least one further analyte from the spectrum recorded by the detector device,
   wherein the measurement light source is a polychromatic LED, which for determining the hemoglobin derivatives emits measurement radiation in at least one spectral region B in which the hemoglobin derivatives exhibit significant absorbance, and which for determining said at least one further analyte emits measurement radiation in at least one other spectral region A in which the at least one further analyte exhibits significant absorbance.

2. The oximeter according to claim 1, wherein the measurement light source is a luminescence conversion LED comprising at least one primary emitter and at least one secondary emitter, the primary emitter emitting measurement radiation in the spectral region A and the secondary emitter emitting measurement radiation in the spectral region B.

3. The oximeter according to claim 1, wherein the measurement light source comprises a plurality of light emitting layers With different emission spectra, where at least one of the light emitting layers emits measurement radiation in the spectral region A and at least one other light emitting layer emits measurement radiation in the spectral region B, and where the light emitting layers are arranged within the measurement light source in such a way that the measurement radiation has an essentially homogeneous spectrum across that part of the output surface of the measurement light source which is utilized for measurement.

4. The oximeter according to claim 3, wherein the measurement light source comprises a plurality of light emitting layers with different emission spectra, which layers are at least partially transparent and are stacked one above the other.

5. The oximeter according to claim 1, wherein the measurement light source comprises a plurality of light emitting layers with different emission spectra, where at least one of the light emitting layers emits measurement radiation in spectral region A and at least one other light emitting layer emits measurement radiation in spectral region B, and where the light emitting layers are arranged within the measurement light source in such a way that the measurement radiation has an essentially homogeneous spectrum over that angle range of the output radiation of the measurement light source which is utilized for measurement.

6. The oximeter according to claim 5, wherein the measurement light source comprises a plurality of light emitting layers with different emission spectra, which layers are at least partially transparent and are stacked one above the other.

7. The oximeter according to claim 1, wherein said further analyte is bilirubin and the spectral region A of the measurement radiation lies in the range of 450-500 nm.

8. The oximeter according to claim 1, wherein the spectral region B of the measurement radiation lies in the range of 520-670 nm.

9. The oximeter according to claim 1, wherein the spectral region A and the spectral region B of the measurement radiation are separated by a region of lesser intensity.

10. The oximeter according to claim 1, wherein further optical components are provided for propagation of the measurement radiation between the measurement light source and the sample chamber and/or between the sample chamber and the detector device.

11. The oximeter according to claim 1, wherein filter elements for further spectral adaptation of the measurement radiation are provided between the measurement light source and the sample chamber and/or between the sample chamber and the detector device.

12. The oximeter according to claim 1, wherein the detector device includes a polychromator followed by a multi-channel detector unit.

13. The oximeter according to claim 12, wherein said multi-channel detector is a detector array which simultaneously records all measurement wavelengths.

14. An oximeter for spectro-photometric in-vitro determination of hemoglobin derivatives and at least one further analyte in a sample comprising:
   a single measurement light source, which emits measurement radiation, being directed to a sample chamber containing said sample,
   a detector device, which records a spectrum of the measurement radiation after its interaction with said sample, and
   an evaluation unit following the detector device, which determines the hemoglobin derivatives and at least one further analyte from the spectrum recorded by the detector device,
   wherein the measurement light source is a luminescence conversion LED comprising at least one primary emitter and at least one secondary emitter, the primary emitter emitting measurement radiation in a spectral region A, in which the at least one further analyte exhibits significant absorbance, and the secondary emitter emitting measurement radiation in a spectral region B in which the hemoglobin derivatives exhibit significant absorbance.

15. The oximeter according to claim 14, wherein said further analyte is bilirubin and the spectral region A of the measurement radiation lies in the range of 450-500 nm.

16. The oximeter according to claim 14, wherein the spectral region B of the measurement radiation lies in the range of 520-670 nm.

17. The oximeter according to claim 14, wherein the spectral region A and the spectral region B of the measurement radiation are separated by a region of lesser intensity.

18. The oximeter according to claim 14, wherein further optical components are provided for propagation of the measurement radiation between the measurement light source and the sample chamber and/or between the sample chamber and the detector device.

19. The oximeter according to claim 14, wherein filter elements for further spectral adaptation of the measurement radiation are provided between the measurement light source and the sample chamber and/or between the sample chamber and the detector device.

20. The oximeter according to claim 14, wherein the detector device includes a polychromator followed by a multi-channel detector unit.

21. The oximeter according to claim 20, wherein said multi-channel detector is a detector array which simultaneously records all measurement wavelengths.

22. An oximeter for spectro-photometric in-vitro determination of hemoglobin derivatives and at least one further analyte in a sample comprising:
   a single measurement light source, which emits measurement radiation, being directed to a sample chamber containing said sample,
   a detector device, which records a spectrum of the measurement radiation after its interaction with said sample, and
   an evaluation unit following the detector device, which determines the hemoglobin derivatives and at least one further analyte from the spectrum recorded by the detector device,
wherein the measurement light source comprises a plurality of light emitting layers with different emission spectra, where at least one of the light emitting layers emits measurement radiation in a spectral region A, in which the at least one further analyte exhibits significant absorbance, and at least one other light emitting layer emits measurement radiation in a spectral region B, in which the hemoglobin derivatives exhibit significant absorbance, and where the light emitting layers are arranged within the measurement light source in such a way that the measurement radiation has an essentially homogeneous spectrum across that part of the output surface of the measurement light source which is utilized for measurement.

* * * * *